United States Patent
Jin et al.

(10) Patent No.: US 9,981,078 B2
(45) Date of Patent: May 29, 2018

(54) LEFT VENTRICULAR ASSIST DEVICE

(71) Applicants: Lijun Jin, Guangdong (CN); APT MEDICAL HUNAN INC, Hunan (CN)

(72) Inventors: Lijun Jin, Guangdong (CN); Zhenghui Cheng, Hunan (CN); Shiping Yan, Hunan (CN)

(73) Assignees: Lijun Jin, Guangzhou (CN); APT MEDICAL HUNAN INC, Xiangxiang (CN)

( * ) Notice: Subject to any disclaimer, the term of this patent is extended or adjusted under 35 U.S.C. 154(b) by 286 days.

(21) Appl. No.: 15/022,801

(22) PCT Filed: Sep. 28, 2014

(86) PCT No.: PCT/CN2014/087651
§ 371 (c)(1),
(2) Date: Mar. 17, 2016

(87) PCT Pub. No.: WO2016/041220
PCT Pub. Date: Mar. 24, 2016

(65) Prior Publication Data
US 2016/0296683 A1 Oct. 13, 2016

(30) Foreign Application Priority Data

Sep. 15, 2014 (CN) .......................... 2014 1 0468040
Sep. 15, 2014 (CN) ..................... 2014 2 0528554 U

(51) Int. Cl.
*A61M 1/00* (2006.01)
*A61M 1/10* (2006.01)
(Continued)

(52) U.S. Cl.
CPC ........ *A61M 1/1074* (2014.02); *A61M 1/1008* (2014.02); *A61M 1/1096* (2014.02);
(Continued)

(58) Field of Classification Search
CPC .......................... A61M 1/1074; A61M 1/1008
(Continued)

(56) References Cited

U.S. PATENT DOCUMENTS 3,504,662 A  4/1970  Jones
3,592,184 A  7/1971  Klink et al.
(Continued)

FOREIGN PATENT DOCUMENTS

CN  201067570 Y  6/2008
CN  102488955 A  6/2012
(Continued)

OTHER PUBLICATIONS

International Search Report for PCT/CN2014/087651 dated Jun. 30, 2015, 11 pages.

*Primary Examiner* — Nadia A Mahmood
(74) *Attorney, Agent, or Firm* — RMCK Law Group, PLC

(57) ABSTRACT

A left ventricular assist device includes an outer tube, which includes a ventricle section located in the left ventricle and an artery section located in the aorta, the ventricle section is provided with first suction meshes, and the artery section is provided with first discharge meshes, and the outer tube is in communication with an external drive device; a ventricular-side suction component provided in the ventricle section; and a discharge-section balloon catheter, is provided with second discharge meshes, and the second discharge meshes and the first discharge meshes are arranged to be staggered and not overlapped. With the suction and inflating of the external drive device, blood is sucked into the outer tube from the left ventricle by the ventricular-side suction component, and forced out of the outer tube into the aorta by the discharge-section balloon catheter, to pump blood in the left ventricle into the aorta.

20 Claims, 8 Drawing Sheets

(51) Int. Cl.
    *A61M 25/00*     (2006.01)
    *A61M 25/09*     (2006.01)
    *A61M 1/12*     (2006.01)

(52) U.S. Cl.
    CPC ............ *A61M 1/122* (2014.02); *A61M 1/125* (2014.02); *A61M 25/005* (2013.01); *A61M 25/0045* (2013.01); *A61M 25/0097* (2013.01); *A61M 25/09* (2013.01); *A61M 1/12* (2013.01); *A61M 2205/0238* (2013.01)

(58) Field of Classification Search
    USPC .......................................................... 600/18
    See application file for complete search history.

(56) References Cited

U.S. PATENT DOCUMENTS

| | | |
|---|---|---|
| 3,692,018 A | 9/1972 | Goetz et al. |
| 4,014,317 A | 3/1977 | Bruno |
| 4,301,797 A | 11/1981 | Pollack |
| 4,861,330 A | 8/1989 | Voss |
| 5,928,132 A | 7/1999 | Leschinsky |
| 6,132,364 A | 10/2000 | Rottenberg et al. |
| 6,136,025 A | 10/2000 | Barbut et al. |
| 2008/0306328 A1 | 12/2008 | Ercolani et al. |
| 2012/0053392 A1 | 3/2012 | Kung |

FOREIGN PATENT DOCUMENTS

| | | |
|---|---|---|
| CN | 204147329 U | 2/2015 |
| WO | 2012158437 A2 | 11/2012 |

US 9,981,078 B2

LEFT VENTRICULAR ASSIST DEVICE

The present application is the national phase of International Application No. PCT/CN2014/087651, titled "LEFT VENTRICULAR ASSIST DEVICE", filed on Sep. 28, 2014, which claims the benefit of priorities to Chinese patent application No. 201410468040.9 titled "LEFT VENTRICULAR ASSIST DEVICE" and filed with the Chinese State Intellectual Property Office on Sep. 15, 2014, and Chinese patent application No. 201420528554.4 titled "LEFT VENTRICULAR ASSIST DEVICE" and filed with the Chinese State Intellectual Property Office on Sep. 15, 2014, the entire disclosures of which are incorporated herein by reference.

FIELD

The present application relates to the technical field of interventional medical equipment, in particular to a left ventricular assist device.

BACKGROUND

In recent years, the incidence of cardiovascular disease has increased. According to the investigation made by the World Health Organization, at present, cardiovascular diseases account for about 30% of all diseases, and are expected to account for 40% of all diseases in 2020. Most of the cardiovascular diseases ultimately affect the function of the left ventricle, resulting in diseases affecting the function of the left ventricle, such as left ventricular failure, and cardiogenic shock.

In view of diseases affecting the function of the left ventricle, domestic and foreign scholars propose new methods. Left ventricular assist devices (abbreviated as LVAD) are used for patients with left ventricular dysfunction to drain blood in the left ventricle into the aorta, to provide a circulatory support. The LVAD can be divided into an implantable LVAD and a body-side LVAD according to whether the LVAD is implanted in the body, and can be divided into a pulsatile LVAD and an axial-flow LVAD according to the flow form of blood.

A traditional left ventricular assist device is implanted by surgical procedures. A passage is established between the left ventricle and the aorta by perforating the left ventricle and the aorta and arranging a pump between them.

Surgical implantation will cause a large operation wound. At present, the most commonly used percutaneous left ventricular assist devices in clinic applications mainly include an Extracorporeal membrane oxygenation (abbreviated as Ecmo) system, an intra-aortic balloon counter pulsation (abbreviated as IABP), a Tandem Heart percutaneous left ventricular assist device and an Impella ventricular assist system. In the Ecmo system, two cannulas are implanted into the aorta and the main vein respectively, the cannula in the main vein is connected to an external artificial lung, and the external artificial lung is connected to the cannula in the aorta via an axial-flow pump or a pulsatile pump. The disadvantage of the Ecmo system is that the external artificial lung is required, which causes complex structure and interruption of pulmonary circulation, and thus it is apt to cause pulmonary intravascular thrombosis and massive hemorrhage. In the intra-aortic balloon counter pulsation, a long balloon is inserted into the aorta, and the balloon is inflated and deflated with the beating of the heart to increase the myocardial blood supply. The disadvantage of the intra-aortic balloon counter pulsation is that it depends on the function of the ventricle, and thus its operation is not stable.

The Tandem Heart system is comprised of an inflow cannula punctured into the left atrium via the femoral vein, an extracorporeal central pump and an outflow cannula punctured into the left ventricle via the femoral artery, thus a drainage channel is established from the left atrium to the femoral artery. The disadvantages of the Tandem Heart system are that there are two large wounds, the operation is complicated and an atrial septal puncture is required. The Impella system is comprised of a cannula punctured into the left ventricle via the femoral artery, a cage-shaped blood inlet is provided at a front end of the cannula, a blood outlet is provided at the ascending aorta, and an axial pump is provided between the inlet and the outlet to drain blood in the left ventricle into the aorta. The disadvantage of the Impella system is that the flow depends on a rotating speed of the pump, and blades rotating in high speed may damage red blood cells and so on.

In conclusion, an issue to be addressed by the person skilled in the art is to solve the problems, under the premise of achieving the left ventricle assisting function, that the existing left ventricular assist device has a complex structure, is complicated to operate, and may cause large wounds to human tissue cells, and the operation thereof is unstable.

SUMMARY

In view of this, an object of the present application is to provide a left ventricular assist device, to simplify the structure and operation, increase the stability of operation and reduce the wounds to human tissue and cells under the premise of achieving the left ventricle assisting function.

In order to achieve the above object, the following technical solutions are provided according to the present application.

A left ventricular assist device includes an outer tube, which includes a ventricle section configured to be located in the left ventricle and an artery section configured to be located in the aorta, wherein a tube wall of the ventricle section is provided with first suction meshes, a tube wall of the artery section is provided with first discharge meshes, and the outer tube has one end closed and another end configured to be in communication with an external drive device; a ventricular-side suction component arranged in the ventricle section, wherein, the ventricular-side suction component is configured to drain blood in the left ventricle into a chamber of the outer tube in a case that the external drive device performs suction, and configured to prevent blood in the outer tube from being forced out of the ventricle section in a case that the external drive device performs inflating process: and a discharge-section balloon catheter, wherein two ends of the discharge-section balloon catheter are hermetically sleeved and fixed on an outer wall of the artery section, a tube wall of the discharge-section balloon catheter is provided with second discharge meshes, and the second discharge meshes and the first discharge meshes are arranged to be staggered with respect to each other and are not overlapped, and in a case that the external drive device performs suction, the discharge-section balloon catheter is configured to hermetically fit onto the outer wall of the artery section, and in a case that the external drive device performs inflating process, the discharge-section balloon catheter is configured to be disengaged from the outer wall of the artery section to form a gap.

Preferably, in the left ventricular assist device, the ventricular-side suction component is a suction-section balloon catheter, two ends of the suction-section balloon catheter are hermetically fixed on an inner wall of the ventricle section, the suction-section balloon catheter is provided with second suction meshes, and the second suction meshes and the first suction meshes are arranged to be staggered with respect to each other and are not overlapped. The suction-section balloon catheter is made of ductile materials. In a case that the external drive device performs suction, a gap is formed between the suction-section balloon catheter and the inner wall of the ventricle section, and in a case that the external drive device performs inflating process, the suction-section balloon catheter is configured to hermetically fit onto the inner wall of the ventricle section.

Preferably, in the left ventricular assist device, the ventricular-side suction component is a one-way valve provided in the ventricle section and between the ventricle section and the artery section, and a one-way communicating direction of the one-way valve is directed from the ventricle section to the artery section.

Preferably, the left ventricular assist device further includes a joint connected to a distal end, away from the heart, of the outer tube, and the joint is configured to be connected to the external drive device.

Preferably, in the left ventricular assist device, the joint includes a first branch tube and a second branch tube, and the first branch tube is connected to the external drive device. The left ventricular assist device further includes a guide wire chamber, the guide wire chamber runs through the interior of the outer tube, a proximal end, close to the heart, of the guide wire chamber is hermetically fixed to a proximal end, close to the heart, of the outer tube and extends out of the proximal end of the outer tube, and a distal end, away from the heart, of the guide wire chamber is hermetically fixed to an end of the second branch tube and is in communication with the outside.

Preferably, the left ventricular assist device further includes a guide wire chamber fixed to an outer wall of a proximal end, close to the heart, of the outer tube.

Preferably, in the left ventricular assist device, the proximal end of the guide wire chamber has a circular structure curved towards the distal end of the guide wire chamber.

Preferably, the left ventricular assist device further includes a developing indicator provided on the outer tube and between the ventricle section and the artery section.

Preferably, in the left ventricular assist device, the outer tube has a single-layer structure, the single-layer structure is a metal mesh tube; or, the outer tube has a multilayer structure, the multilayer structure includes an inner layer, a middle layer and an outer layer sequentially from the inside to the outside, and the inner layer is a polytetrafluoroethylene film, the middle layer is a steel wire net or spring, and the outer layer is a nylon layer.

Preferably, in the left ventricular assist device, an included angle between the ventricle section and the artery section of the outer tube ranges from 135 degrees to 155 degrees.

Compared with the conventional technology, the present application has the following beneficial effects.

In the left ventricular assist device of the present application, the ventricular-side suction component is provided in the ventricle section of the outer tube, and the two ends of the discharge-section balloon catheter are hermetically sleeved on the outer wall of the artery section of the outer tube. The left ventricular assist device is punctured into the heart to locate the ventricle section of the outer tube in the left ventricle and locate the artery section of the outer tube in the aorta, and the ventricle section and the artery section are separated by the aortic valve between left ventricle and the aorta, and thus will not interfering with each other. In operation, when the external drive device performs suction, a negative pressure is formed in the outer tube. Under the action of the negative pressure, the discharge-section balloon catheter is sucked to fit close with the outer wall of the artery section. Since the second discharge meshes and the first discharge meshes are arranged to be staggered and not overlapped, the first discharge meshes on the artery section are closed by the discharge-section balloon catheter, thus the artery section of the outer tube is not in communication with the aorta. At the same time, under the action of suction of the external drive device, blood in the left ventricle is sucked into the ventricle section of the outer tube by the ventricular-side suction component and flows into the whole chamber of the outer tube. After this, when the external drive device inflates the outer tube, the ventricular-side suction component prevents the blood in the outer tube from being discharged to the left ventricle from the ventricle section. At the same time, under the action of the inflating, the discharge-section balloon catheter is disengaged from the artery section to form a communicating gap between them, thus the first discharge meshes and the second discharge meshes are in communication with each other, and blood flows into the aorta from the artery section of the outer tube. One circulation is achieved by the suction and inflating processes of the external drive device, to pump blood in the left ventricle into the aorta. The left ventricular assist device of the present application does not require other components such as an artificial lung, thus having a simple structure; and the device will not stop operating due to an interruption of the pulmonary circulation, thus having an improved reliability; and with the device, it only needs to open one puncture in the body, which causes a small wound to the body and will not damage the blood cells.

BRIEF DESCRIPTION OF THE DRAWINGS

For more clearly illustrating embodiments of the present application or the technical solutions in the conventional technology, drawings referred to describe the embodiments or the conventional technology will be briefly described hereinafter. Apparently, the drawings in the following description are only some examples of the present application, and for the person skilled in the art, other drawings may be obtained based on these drawings without any creative efforts.

REFERENCE NUMERALS IN FIG. 1 TO 10

Figure 1:
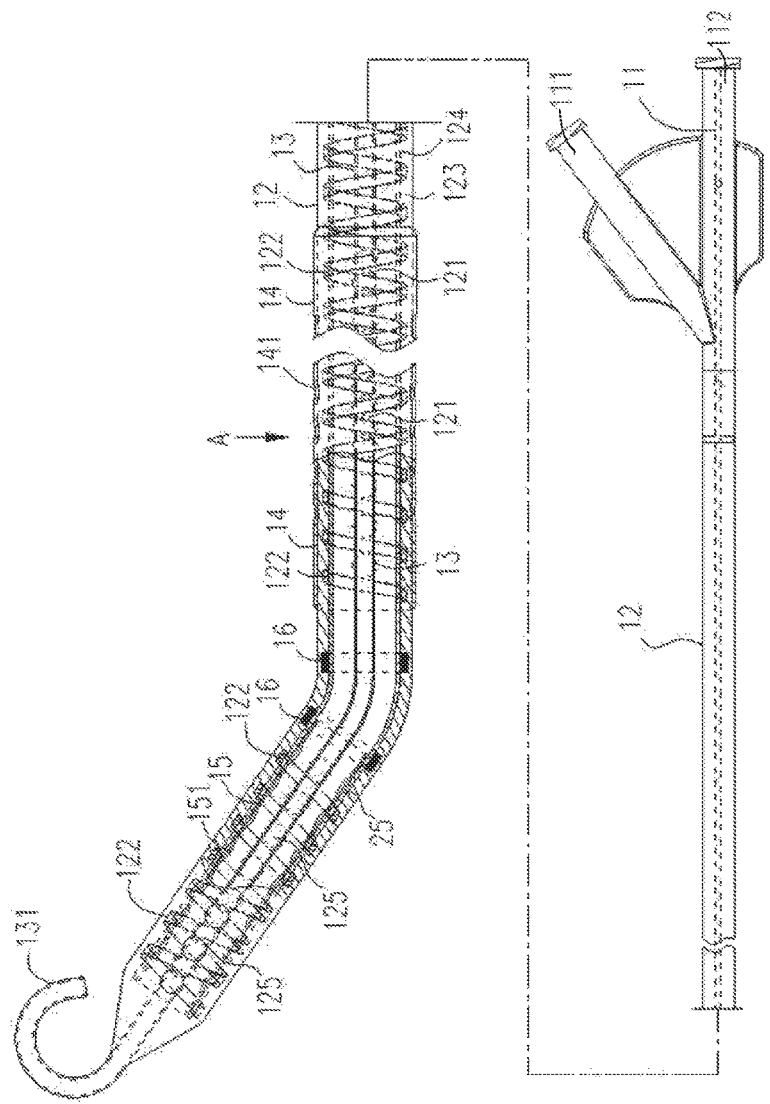
FIG. 1 is a schematic view showing the structure of a first kind of left ventricular assist device according to an embodiment of the present application.
Figure 2:
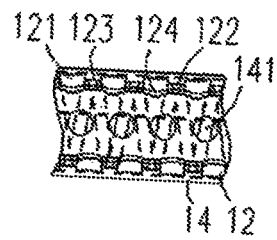
FIG. 2 is a partial schematic view of FIG. 1 viewed in direction A.

| 11 joint, | 111 first branch tube, |
|---|---|
| 112 second branch tube, | 12 outer tube, |
| 121 first discharge mesh, | 122 middle layer, |
| 123 outer layer, | 124 inner layer, |
| 125 first suction mesh, | 13 guide wire chamber, |
| 131 circular structure, | 14 discharge-section balloon catheter, |
| 141 second discharge mesh, | 15 suction-section balloon catheter, |
| 151 second suction mesh, | 16 developing indicator, and |
| 18 one-way valve. | |

DETAILED DESCRIPTION

The core of the present application is to provide a left ventricular assist device, which simplifies the structure and operation, increases the stability of operation and reduces the wounds to human tissue and cells under the premise of achieving the left ventricle assisting function.

The technical solutions in the embodiments of the present application will be described clearly and completely hereinafter in conjunction with the drawings in the embodiments of the present application. Apparently, the described embodiments are only a part of the embodiments of the present application, rather than all embodiments. Based on the embodiments in the present application, all of other embodiments, made by the person skilled in the art without any creative efforts, fall into the scope of the present application.

Referring to FIGS. 1 to 10, the embodiments of the present application provide a left ventricular assist device, including an outer tube 12, a ventricular-side suction component and a discharge-section balloon catheter 14. The outer tube 12 includes a ventricle section and an artery section adjacent to each other; the outer tube 12 is hard and has good radial compressive property. In using, the ventricle section is located inside the left ventricle, and the artery section is located inside the aorta. A tube wall of the ventricle section is provided with first suction meshes 125, and the artery section is provided with first discharge meshes 121. The outer tube 12 has one end closed and another end configured to be in communication with an external drive device, and the external drive device provides a suction force and an inflating force. The ventricular-side suction component is provided in the ventricle section, and when the external drive device performs suction, the ventricular-side suction component drains blood in the left ventricle into a chamber of the outer tube 12; and when the external drive device performs inflating process, the ventricular-side suction component prevents the blood in the outer tube from being forced out of the ventricle section into the left ventricle. Both ends of the discharge-section balloon catheter 14 are hermetically sleeved and fixed on an outer wall of the artery section, thus all of the first discharge meshes 121 are covered by the discharge-section balloon catheter 14. A tube wall of the discharge-section balloon catheter 14 is provided with second discharge meshes 141. The second discharge meshes 141 and the first discharge meshes 121 are arranged to be staggered with respect to each other and not overlapped. The discharge-section balloon catheter 14 is made of medical materials with good tensile property, and is very thin and very soft. When the external drive device performs suction, the discharge-section balloon catheter 14 contracts to hermetically fit onto the outer wall of the artery section, thus the first discharge meshes 121 are not in communication with the second discharge meshes 141. When the external drive device performs inflating process, the discharge-section balloon catheter 14 expands to be disengaged from the outer wall of the artery section to form a gap between the discharge-section balloon catheter 14 and the outer wall of the artery section, thus the first discharge meshes 121 are in communication with the second discharge meshes 141.

The operating process and principle of the left ventricular assist device are described as follows. During operation, the left ventricular assist device is washed with heparin saline and then deflated, the outer tube 12 is connected to the external drive device, a chamber, connected to the inner chamber of the outer tube 12, of the external drive device is washed with heparin saline and is filled with heparin saline and then deflated. After the completion of necessary work for the operation, a guide wire is placed into the aorta via a sheath at a femoral artery puncture site and finally into the left ventricle, to allow the ventricle section of the outer tube 12 to be located in the left ventricle and the artery section of the outer tube 12 to be located in the aorta, and the ventricle section and the artery section are separated by an aortic valve between the left ventricle and the aorta. In using, when the external drive device performs suction, a negative pressure is formed in the outer tube 12, and under the action of the negative pressure, the discharge-section balloon catheter 14 is sucked to contract, to fit close to the outer wall of the artery section. Since the second discharge meshes 141 and the first discharge meshes 121 are arranged to be staggered with respect to each other and are not overlapped, the first discharge meshes 121 on the artery section are closed by the discharge-section balloon catheter 14, and the first discharge meshes 121 are not in communication with the second discharge meshes 141, thus the artery section of the outer tube 12 is not in communication with the aorta, and blood in the aorta will not flow into the outer tube 12. At the same time, under the action of suction of the external drive device, blood in the left ventricle is sucked into the ventricle section of the outer tube 12 by the ventricular-side suction component and enters into the whole tube chamber of the outer tube 12 and the chamber of the external drive device. This process completes an operation of leading blood into the outer tube 12 from the left ventricle. After this, the external drive device inflates the outer tube 12, the ventricular-side suction component prevents the blood in the outer tube 12 from being forced out of the ventricle section into the left ventricle; and at the same time, under the action of the inflating, the discharge-section balloon catheter 14 expands, thus the tube wall of the discharge-section balloon catheter 14 is disengaged from the outer wall of the artery section, to form a communicating gap between the discharge-section balloon catheter 14 and the outer wall of the artery section. Thus the first discharge meshes 121 are in communication with the second discharge meshes 141, and the blood enters into the aorta from the artery section of the outer tube 12. This process completes an operation of leading blood into the aorta from the outer tube 12. One circulation is achieved by the suction and inflating processes of the external drive device to pump blood in the left ventricle into the aorta.

It can be seen that the left ventricular assist device of the present application does not require components such as an artificial lung, thus having a simple structure; and the device will not stop operating due to an interruption of the pulmonary circulation, thus having an improved reliability. With this device, it only needs to open one puncture in the body, which causes a little wound to the body and will not cause damage to blood cells. The external drive device may adjust the frequencies of suction and inflating processes according to the actual pulse frequency of human to realize the frequency synchronization, thereby achieving the left ventricle assisting function.

Figure 3:
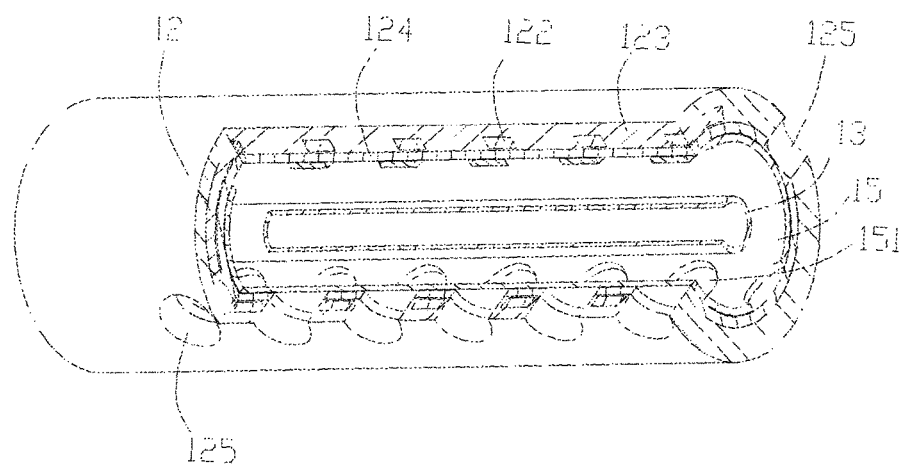
FIG. 3 is a schematic view showing the structure of a suction-section balloon catheter and a ventricle section of an outer tube of the left ventricular assist device in FIG. 1.
Figure 4:
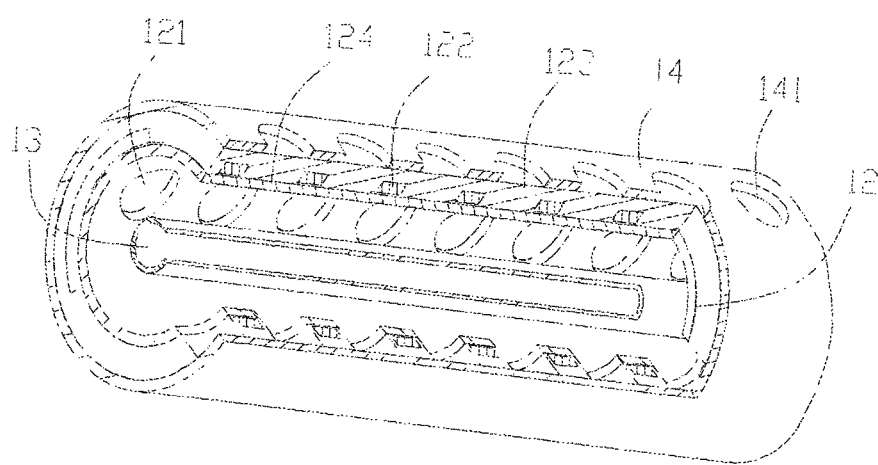
FIG. 4 is a schematic view showing the structure of a discharge-section balloon catheter and an artery section of the outer tube of the left ventricular assist device in FIG. 1.

As shown in FIGS. 1 to 7, in a specific embodiment of the present application, the ventricular-side suction component may be a suction-section balloon catheter 15. The suction-section balloon catheter 15 is provided inside the ventricle section, and having two ends hermetically fixed on an inner wall of the ventricle section, thus the first suction meshes 125 are covered by the suction-section balloon catheter 14. The suction-section balloon catheter 15 is provided with second suction meshes 151. The second suction meshes 151 and the first suction meshes 125 are arranged to be staggered with respect to each other and are not overlapped. The suction-section balloon catheter 15 is made of medical materials with good tensile property, and is also very thin and very soft. The specific structure is shown in FIG. 3.

In the operation of the suction-section balloon catheter 15, when the external drive device performs suction, a negative pressure is formed in the outer tube 12, the suction-section balloon catheter 15 contracts under the action of suction of the negative pressure, and the percentage of contraction of the suction-section balloon catheter 15 is greater than that of the outer tube 12, thus a communicating gap is formed between the suction-section balloon catheter 15 and the inner wall of the ventricle section, and the first suction meshes 125 are in communication with the second suction meshes 151. At this time, blood is sucked into the ventricle section from the left ventricle and flows into the whole tube chamber of the outer tube 12 and the external drive device. When the external drive device performs inflating process, the suction-section balloon catheter 15 expands to hermetically fit onto the inner wall of the ventricle section, thus the first suction meshes 125 are not in communication with the second suction meshes 151, and the blood in the outer tube 12 will not be discharged into the left ventricle via the suction-section balloon catheter 15 in the ventricle section.

Figure 8:
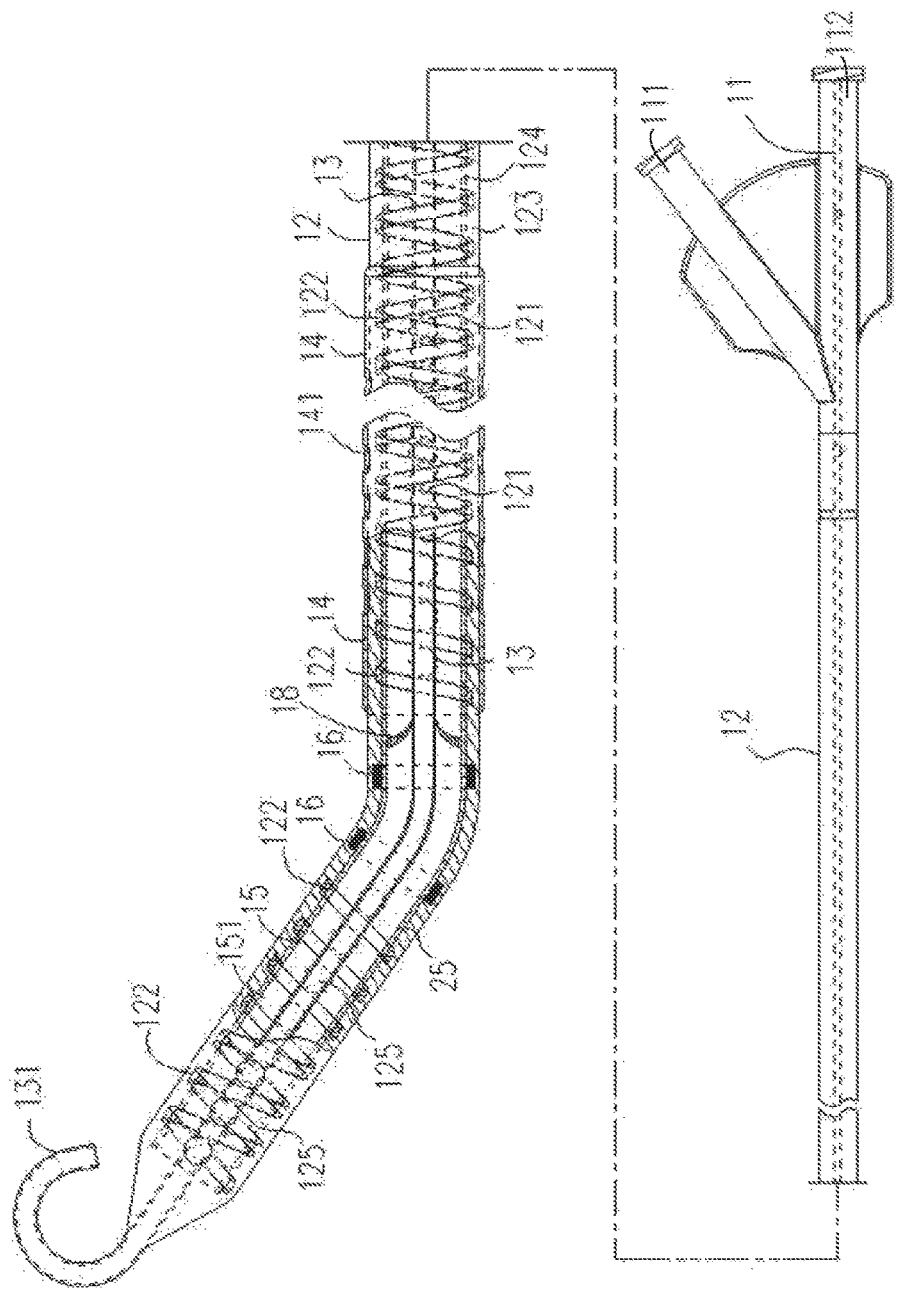
FIG. 8 is a schematic view showing the structure of a fourth kind of left ventricular assist device according to an embodiment of the present application.
Figure 9:
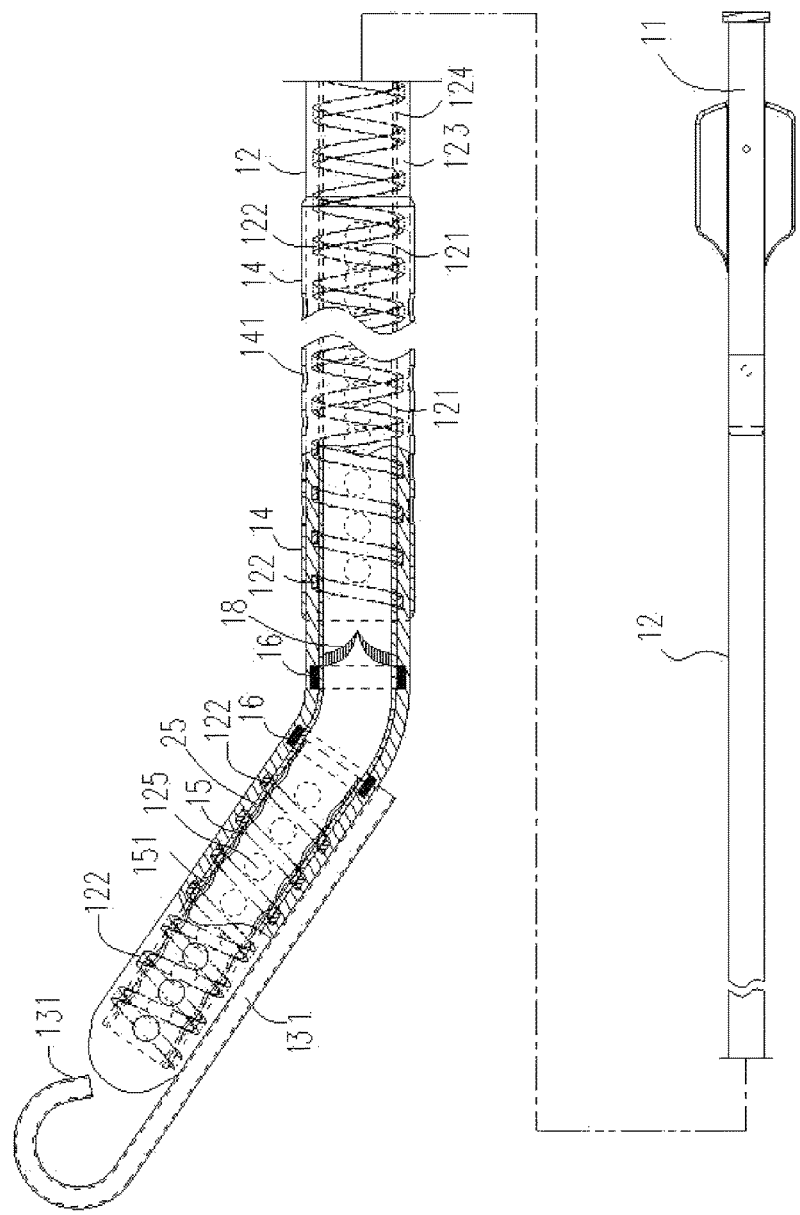
FIG. 9 is a schematic view showing the structure of a fifth kind of left ventricular assist device according to an embodiment of the present application.
Figure 10:
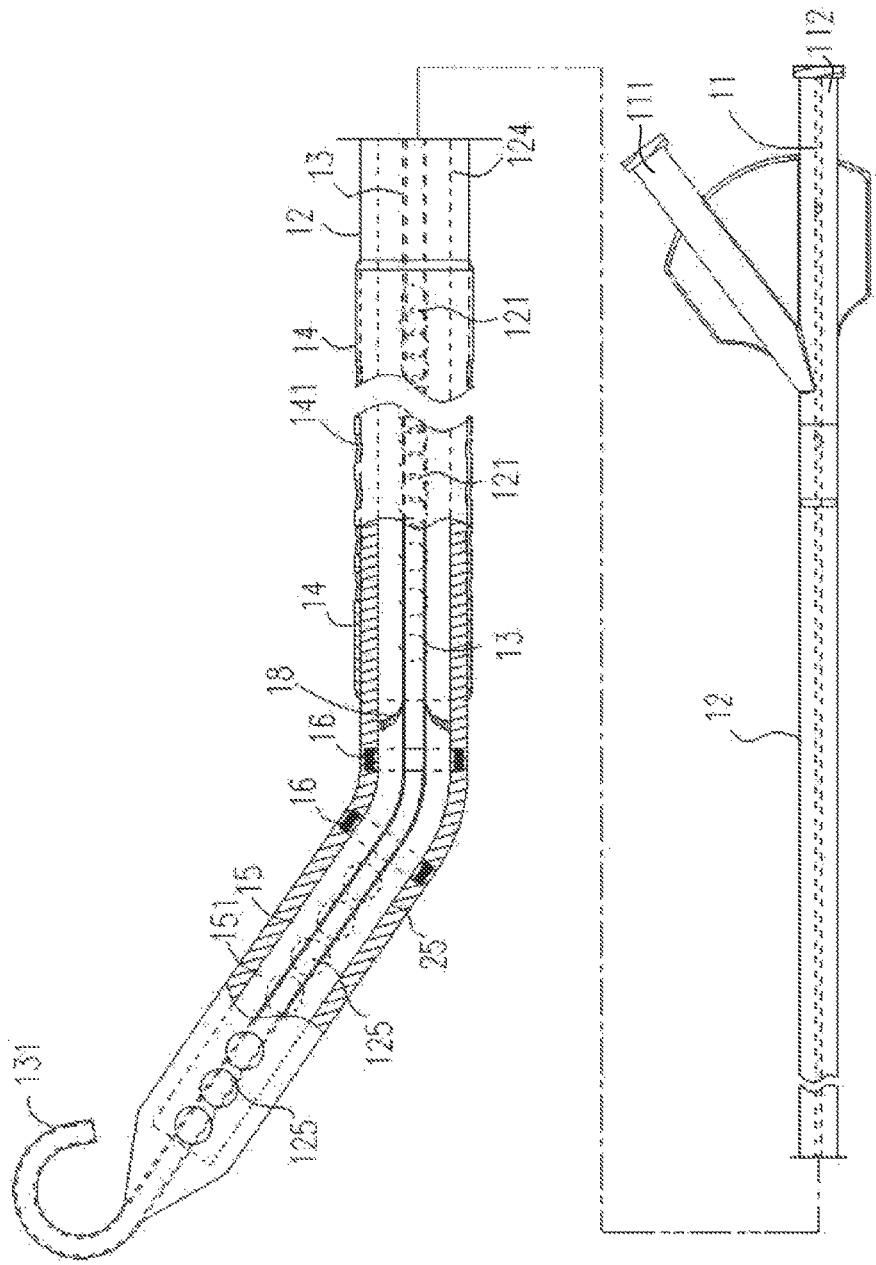
FIG. 10 is a schematic view showing the structure of a sixth kind of left ventricular assist device according to an embodiment of the present application.

As shown in FIGS. 8 to 10, in a specific embodiment of the present application, the ventricular-side suction component may also be a one-way valve 18 provided in the ventricle section and located between the ventricle section and the artery section, and the one-way communicating direction of the one-way valve 18 is directed from the ventricle section to the artery section.

The operating process and principle of the ventricular-side suction component embodied as the one-way valve 18 are descried as follows. When the external drive device performs suction, a negative pressure is formed in the outer tube 12, blood is sucked into the ventricle section through the first suction meshes 125 on the ventricle section, and under the action of the suction force, the blood entered into the ventricle section flows into the artery section through the one-way valve 18 arranged between the ventricle section and the artery section, and flows through the entire outer tube 12 and into the chamber of the external drive device. When the external drive device performs inflating process, since the one-way valve 18 has the property of one-way communication which allows blood to flow from the ventricle section to the artery section, the blood is prevented by the one-way valve 18 from flowing to the ventricle section, thus the blood will not flow back to the left ventricle from the ventricle section, and will be only discharged to the aorta through the discharge-section balloon catheter 14, thereby achieving the flow of blood from the left ventricle to the aorta.

As shown in FIGS. 1 to 10, in this embodiment, the left ventricular assist device further includes a joint 11 connected to a distal end, away from the heart, of the outer tube 12, and the joint 11 is configured to be connected to the external drive device. The structural form of the joint 11 may be changed based on different structures of the external drive device and the outer tube 12, and for different structures of the external drive device and the outer tube 12, it is only required to change the joint 11, which increases the applicability of the left ventricular assist device. The joint 11 is an injection part and is made of plastic, and the thread of the joint 11 has a standard luer structure. Of course, the external drive device may also be connected to the outer tube 12 directly.

As shown in FIGS. 1, 6, 8 and 10, in this embodiment, one form of the joint 11 and an installing structure of a guide wire chamber 13 are provided. The joint 11 includes a first branch tube 111 and a second branch tube 112, and the first branch tube 111 is connected to the external drive device. The left ventricular assist device includes the guide wire chamber 13 configured to allow a guide wire to pass through, and with the guidance of the guide wire and the guide wire chamber 13, the left ventricular assist device is led into the aorta via a sheath at a femoral artery puncture site and finally into the left ventricle. The guide wire chamber 13 in this embodiments runs through the interior of the outer tube 12, a proximal end, close to the heart, of the guide wire chamber 13 is hermetically fixed to a proximal end, close to the heart, of the outer tube 12 and extends out of the proximal end of the outer tube 12; a distal end, away from the heart, of the guide wire chamber 13 is hermetically fixed to an end of the second branch tube 112 and is in communication with the outside. This installing structure of the guide wire chamber 13 has a high stability.

Figure 5:
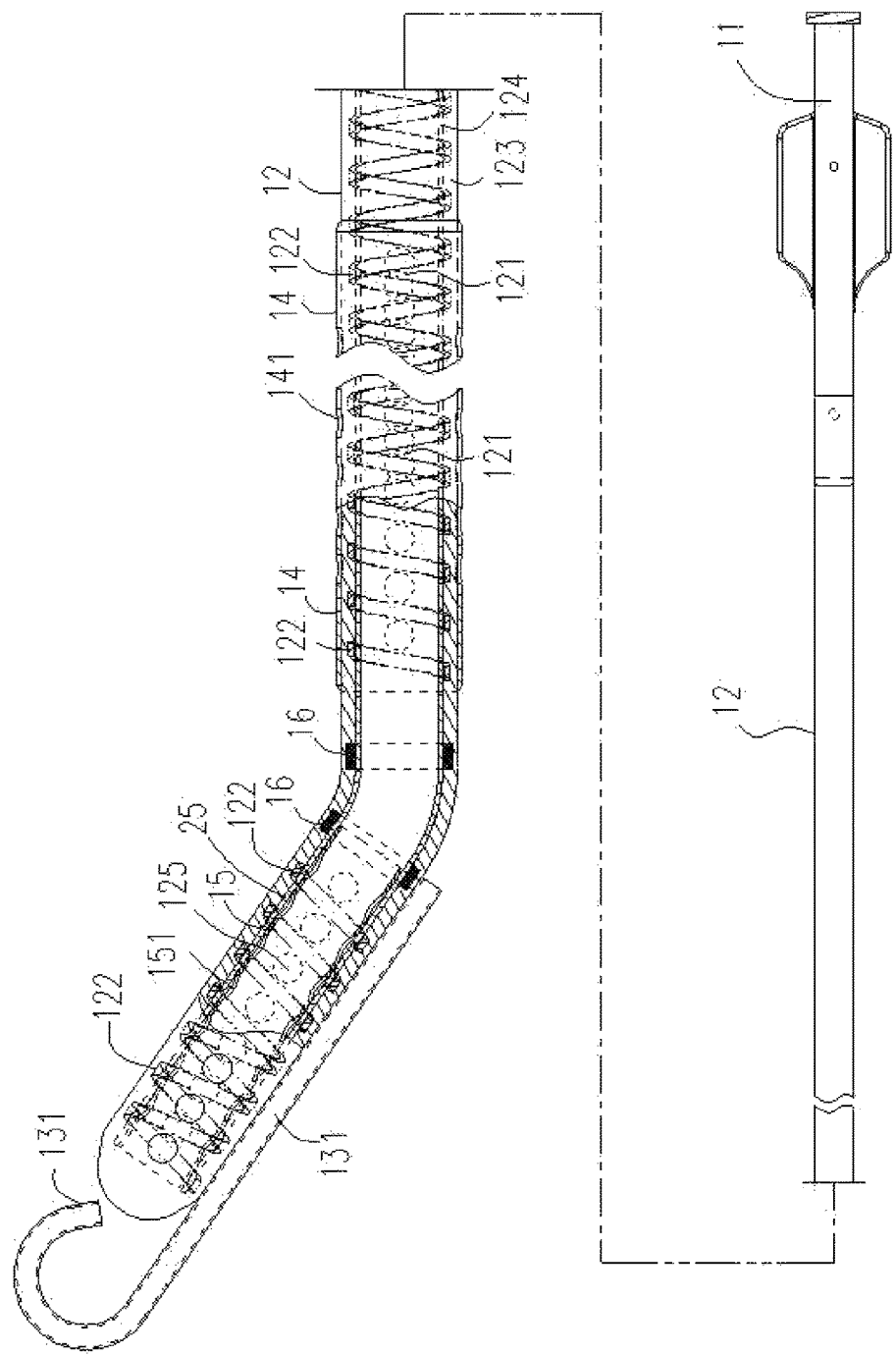
FIG. 5 is a schematic view showing the structure of a second kind of left ventricular assist device according to an embodiment of the present application.

Except for the structures described above, the form of the joint 11 and the installing structure of the guide wire chamber 13 may be embodied as other structures. As shown in FIGS. 5 and 9, the joint 11 has one branch tube directly connected to the external drive device, and the guide wire chamber 13 is fixed to an outer wall of the proximal end of the outer tube 12. Since the guide wire chamber 13 is short, its own hardness has no influence on the bending performance of the whole outer tube 12, thus the guide wire chamber 13 may be punctured in place more flexibly and more quickly, and the guide wire chamber 13 may be replaced directly outside the outer tube 12, which makes the replacement to be more convenient and quick.

A further optimization to the above two kinds of guide wire chambers 13 may be made, as shown in FIGS. 1 to 10, the proximal end of the guide wire chamber 13 has a circular structure 131 curved towards the distal end of the guide wire chamber 13, and the circular structure 131 has a shape similar to the shape of a pigtail. Since the proximate end of the guide wire chamber 13 is configured as the circular structure 131 being curved, in the puncturing process of the guide wire chamber 13, a tip of the guide wire chamber 13 will not cause damage to the human tissue, especially the inner wall of the heart.

In a specific embodiment of the present application, as shown in FIGS. 1 to 10, the left ventricular assist device further includes a developing indicator 16 provided on the outer tube 12 and between the ventricle section and the artery section. The number of the developing indicators 16 is preferably two, and an area between the two developing indicators 16 is an area for stopping the puncture of the left ventricular assist device. The developing indicators 16 are used in the puncturing process of the left ventricular assist device. When the left ventricular assist device enters into the left ventricle through the aorta, the position reached by the left ventricular assist device can be observed via the developing indicators 16. When the two developing indicators 16 are located at two sides of the aortic valve respectively, the puncturing is stopped and the left ventricular assist device is fixed. At this time, the ventricle section of the outer tube 12 has entered into the left ventricle and the artery section is located in the aorta.

As an optimization, the materials of the developing indicator 16 may be platinum-iridium alloy, gold and so on, and the position of the developing indicator 16 can be observed by a developing apparatus such as X-ray.

As shown in FIGS. 1 to 4, in this embodiment, the outer tube 12 has a multilayer structure, may has a three-layer structure made by rheoforming, and including an inner layer 124, a middle layer 122 and an outer layer 123 sequentially from the inside to the outside. The inner layer 124 is a polytetrafluoroethylene film, and has the advantages of low friction coefficient, good biocompatibility, good lubrication performance, and will not damage the tissue cells. The middle layer 122 is a steel wire net or spring, which can keep the outer tube 12 from being deformed radially in the process of suction and compression, and has a good radial compressive property, and can also improve the advancing performance of the device. The outer layer 123 is a nylon layer, made of materials such as Pebax55D, which has a good plasticity, thus the device has good tracking performance and fracture resistance when bypassing the curved blood vessel.

The outer tube 12 may also have a two-layer structure made by rheoforming, an inner layer is a polytetrafluoroethylene film, and an outer layer is a nylon layer, made of materials such as Pebax63D.

Figure 6:
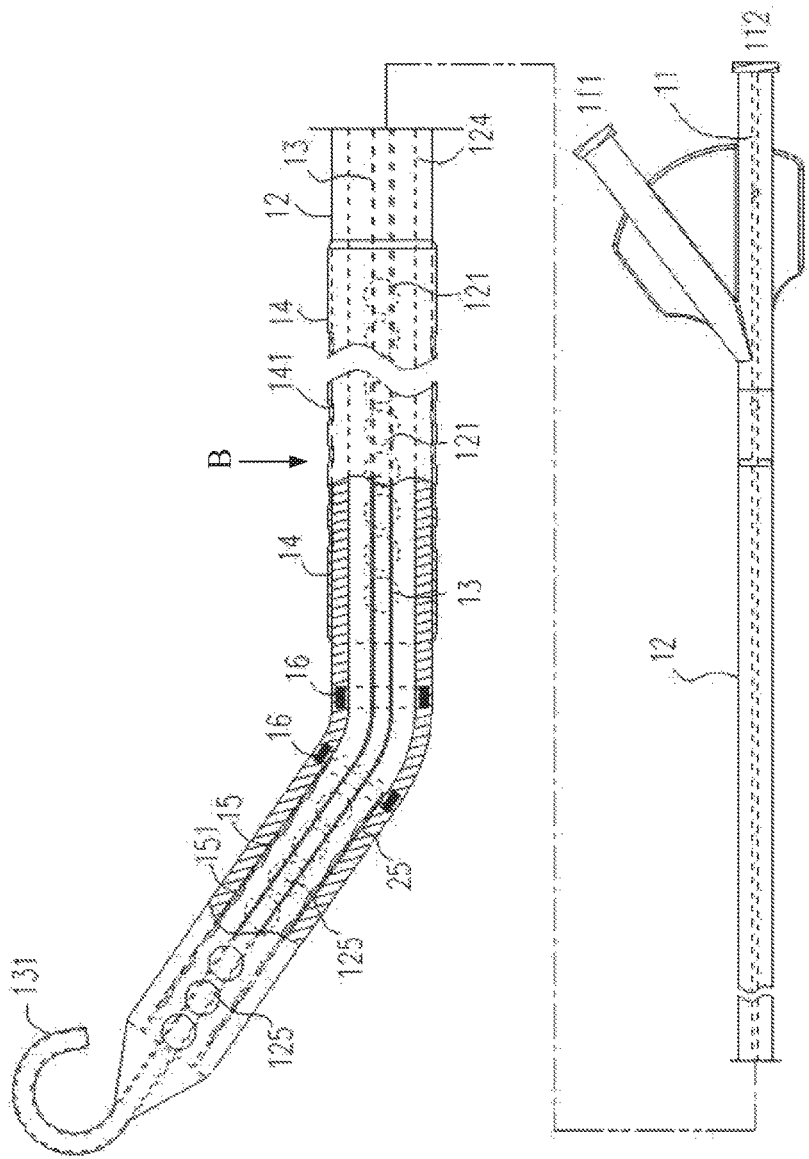
FIG. 6 is a schematic view showing the structure of a third kind of left ventricular assist device according to an embodiment of the present application.
Figure 7:
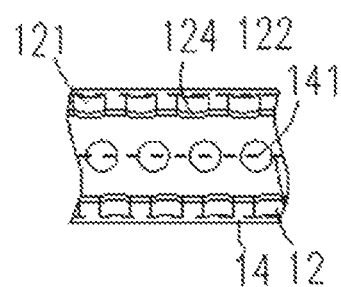
FIG. 7 is a partial schematic view of FIG. 6 viewed in direction B.

Furthermore, the outer tube 12 may also have a single-layer structure, as shown in FIGS. 6, 7 and 10, the single-layer structure is a metal mesh tube. As long as the outer tube has a good radial compressive property and a good passing ability, outer tubes 12 with other materials and structures are also applicable.

As shown in FIGS. 1 to 10, in this embodiment, an included angle between the ventricle section and the artery section of the outer tube 12 ranges from 135 degrees to 155 degrees, preferably 145 degrees. The included angle between the ventricle section and the artery section is determined according to the positional relationship between the heart and the aorta, to allow the outer tube 12 to be inserted into the blood vessel easily. Of course, different included angles may be set according to different structures of the heart, and are not limited to the range and values listed in this embodiment.

In this embodiment, the first suction meshes 125 and the first discharge meshes 121 may be perforated by laser, but also may be directly formed by drilling, the meshes penetrate through the tube wall of the outer tube 12, and there is no burr at the periphery of the meshes, to prevent the formation of small spaces which may cause blood coagulation.

The material of the discharge-section balloon catheter 14 may be nylon material, such as PU8AE, which is easy to deform under pressure, and similar to the balloon in the balloon catheter, the discharge-section balloon catheter 14 may expand when being inflated, and may contract when being deflated. The material of the suction-section balloon catheter 15 may be nylon material, which is easy to deform under pressure. The second suction meshes 151 and the second discharge meshes 141 may be perforated by laser, but also may be directly formed by drilling.

The left ventricular assist device of the present application sucks in blood through the multiple first suction meshes 125 on the outer tube 12 and the second suction meshes 151 on the suction-section balloon catheter 15, and forces out the blood through the multiple second discharge meshes 141 on the discharge-section balloon catheter 14 and the multiple first discharge meshes 121 on the outer tube 12, thereby ensuring the large flow transfer of blood and completely replacing the function of a normal heart, and oxygenated blood is directly sucked from the left ventricle into the aorta, which is consistent with the hemodynamics of the human body.

The left ventricular assist device of the present application is applicable for auxiliary treatments of heart failure, cardiogenic shock, heart pre-transplantation and so on, and for assisting the intervention treatment of complex coronary artery diseases, and may also be used in the emergency treatment of cardiac arrest.

The above embodiments are described in a progressive manner. Each of the embodiments is mainly focused on describing its differences from other embodiments, and references may be made among these embodiments with respect to the same or similar portions among these embodiments.

Based on the above description of the disclosed embodiments, the person skilled in the art is capable of carrying out or using the present application. It is obvious for the person skilled in the art to make many modifications to these embodiments. The general principle defined herein may be applied to other embodiments without departing from the spirit or scope of the present application. Therefore, the present application is not limited to the embodiments illustrated herein, but should be defined by the broadest scope consistent with the principle and novel features disclosed herein.

The invention claimed is:

1. A left ventricular assist device, comprising:
   an outer tube, comprising a ventricle section configured to be located in the left ventricle and an artery section configured to be located in the aorta, wherein a tube wall of the ventricle section is provided with first suction meshes, a tube wall of the artery section is provided with first discharge meshes, and the outer tube has one end closed and another end configured to be in communication with an external drive device;
   a ventricular-side suction component arranged in the ventricle section, wherein, the ventricular-side suction component is configured to drain blood in the left ventricle into a chamber of the outer tube in a case that the external drive device performs suction, and configured to prevent blood in the outer tube from being forced out of the ventricle section in a case that the external drive device performs inflating process; and
   a discharge-section balloon catheter, wherein two ends of the discharge-section balloon catheter are hermetically sleeved and fixed on an outer wall of the artery section, a tube wall of the discharge-section balloon catheter is provided with second discharge meshes, and the second discharge meshes and the first discharge meshes are arranged to be staggered with respect to each other and are not overlapped, and in a case that the external drive device performs suction, the discharge-section balloon catheter is configured to hermetically fit onto the outer wall of the artery section, and in a case that the external drive device performs inflating process, the discharge-section balloon catheter is configured to be disengaged from the outer wall of the artery section to form a gap.

2. The left ventricular assist device according to claim 1, wherein the ventricular-side suction component is a suction-section balloon catheter, two ends of the suction-section balloon catheter are hermetically fixed on an inner wall of the ventricle section, the suction-section balloon catheter is provided with second suction meshes, and the second suction meshes and the first suction meshes are arranged to be staggered with respect to each other and are not overlapped, and in a case that the external drive device performs suction, a gap is formed between the suction-section balloon catheter and the inner wall of the ventricle section, and in a case that the external drive device performs inflating process, the suction-section balloon catheter is configured to hermetically fit onto the inner wall of the ventricle section.

3. The left ventricular assist device according to claim 1, wherein the ventricular-side suction component is a one-way valve provided in the ventricle section and between the ventricle section and the artery section, and a one-way communicating direction of the one-way valve is directed from the ventricle section to the artery section.

4. The left ventricular assist device according to claim 1, further comprising a joint connected to a distal end, away from the heart, of the outer tube, wherein the joint is configured to be connected to the external drive device.

5. The left ventricular assist device according to claim 4, wherein the joint comprises a first branch tube and a second branch tube, and the first branch tube is connected to the external drive device; and the left ventricular assist device further comprises a guide wire chamber, the guide wire chamber runs through the interior of the outer tube, a proximal end, close to the heart, of the guide wire chamber is hermetically fixed to a proximal end, close to the heart, of the outer tube and extends out of the proximal end of the outer tube, and a distal end, away from the heart, of the guide wire chamber is hermetically fixed to an end of the second branch tube and is in communication with the outside.

6. The left ventricular assist device according to claim 4, further comprising a guide wire chamber, wherein the guide wire chamber is fixed to an outer wall of a proximal end, close to the heart, of the outer tube.

7. The left ventricular assist device according to claim 5, wherein the proximal end of the guide wire chamber has a circular structure curved towards the distal end of the guide wire chamber.

8. The left ventricular assist device according to claim 1, further comprising a developing indicator provided on the outer tube and between the ventricle section and the artery section.

9. The left ventricular assist device according to claim 1, wherein the outer tube has a single-layer structure, the single-layer structure is a metal mesh tube; or, the outer tube has a multilayer structure, the multilayer structure comprises an inner layer, a middle layer and an outer layer sequentially from the inside to the outside, and the inner layer is a polytetrafluoroethylene film, the middle layer is a steel wire net or spring, and the outer layer is a nylon layer.

10. The left ventricular assist device according to claim 1, wherein an included angle between the ventricle section and the artery section of the outer tube ranges from 135 degrees to 155 degrees.

11. The left ventricular assist device according to claim 6, wherein the proximal end of the guide wire chamber has a circular structure curved towards the distal end of the guide wire chamber.

12. The left ventricular assist device according to claim 2, further comprising a joint connected to a distal end, away from the heart, of the outer tube, wherein the joint is configured to be connected to the external drive device.

13. The left ventricular assist device according to claim 12, wherein the joint comprises a first branch tube and a second branch tube, and the first branch tube is connected to the external drive device; and the left ventricular assist device further comprises a guide wire chamber, the guide wire chamber runs through the interior of the outer tube, a proximal end, close to the heart, of the guide wire chamber is hermetically fixed to a proximal end, close to the heart, of the outer tube and extends out of the proximal end of the outer tube, and a distal end, away from the heart, of the guide wire chamber is hermetically fixed to an end of the second branch tube and is in communication with the outside.

14. The left ventricular assist device according to claim 12, further comprising a guide wire chamber, wherein the guide wire chamber is fixed to an outer wall of a proximal end, close to the heart, of the outer tube.

15. The left ventricular assist device according to claim 3, further comprising a joint connected to a distal end, away from the heart, of the outer tube, wherein the joint is configured to be connected to the external drive device.

16. The left ventricular assist device according to claim 15, wherein the joint comprises a first branch tube and a second branch tube, and the first branch tube is connected to the external drive device; and the left ventricular assist device further comprises a guide wire chamber, the guide wire chamber runs through the interior of the outer tube, a proximal end, close to the heart, of the guide wire chamber is hermetically fixed to a proximal end, close to the heart, of the outer tube and extends out of the proximal end of the outer tube, and a distal end, away from the heart, of the guide wire chamber is hermetically fixed to an end of the second branch tube and is in communication with the outside.

17. The left ventricular assist device according to claim 15, further comprising a guide wire chamber, wherein the guide wire chamber is fixed to an outer wall of a proximal end, close to the heart, of the outer tube.

18. The left ventricular assist device according to claim 2, wherein the outer tube has a single-layer structure, the single-layer structure is a metal mesh tube; or, the outer tube has a multilayer structure, the multilayer structure comprises an inner layer, a middle layer and an outer layer sequentially from the inside to the outside, and the inner layer is a polytetrafluoroethylene film, the middle layer is a steel wire net or spring, and the outer layer is a nylon layer.

19. The left ventricular assist device according to claim 2, wherein an included angle between the ventricle section and the artery section of the outer tube ranges from 135 degrees to 155 degrees.

20. The left ventricular assist device according to claim 3, wherein the outer tube has a single-layer structure, the single-layer structure is a metal mesh tube; or, the outer tube has a multilayer structure, the multilayer structure comprises an inner layer, a middle layer and an outer layer sequentially from the inside to the outside, and the inner layer is a polytetrafluoroethylene film, the middle layer is a steel wire net or spring, and the outer layer is a nylon layer.

\* \* \* \* \*